(12) United States Patent
Cheang

(10) Patent No.: US 10,582,986 B2
(45) Date of Patent: *Mar. 10, 2020

(54) SYSTEM AND METHOD FOR POSITIONING THREE-DIMENSIONAL BRACKETS ON TEETH

(71) Applicant: ALIGN TECHNOLOGY, INC., San Jose, CA (US)

(72) Inventor: Ka Man Cheang, Sunnyvale, CA (US)

(73) Assignee: ALIGN TECHNOLOGY, INC., San Jose, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/986,305

(22) Filed: May 22, 2018

(65) Prior Publication Data

US 2018/0368942 A1 Dec. 27, 2018

Related U.S. Application Data

(63) Continuation of application No. 15/842,246, filed on Dec. 14, 2017, now Pat. No. 10,022,204, which is a continuation of application No. 14/991,827, filed on Jan. 8, 2016, now Pat. No. 9,844,420, which is a
(Continued)

(51) Int. Cl.
| | |
|---|---|
| *A61C 7/00* | (2006.01) |
| *A61C 7/14* | (2006.01) |
| *G06T 17/20* | (2006.01) |
| *G06T 19/20* | (2011.01) |

(52) U.S. Cl.
CPC .............. *A61C 7/002* (2013.01); *A61C 7/146* (2013.01); *G06T 17/20* (2013.01); *G06T 19/20* (2013.01); *A61C 2007/004* (2013.01); *G06T 2219/2004* (2013.01); *G06T 2219/2021* (2013.01)

(58) Field of Classification Search
CPC ... A61C 7/146; A61C 7/002; A61C 2007/004; G06T 19/00
USPC ......... 433/24, 25, 72, 213; 700/98; 382/128, 382/154, 291; 345/619–682
See application file for complete search history.

(56) References Cited

U.S. PATENT DOCUMENTS

| | | | |
|---|---|---|---|
| 2,467,432 A | 4/1949 | Kesling | |
| 3,407,500 A | 10/1968 | Kesling | |
| 3,600,808 A | 8/1971 | Reeve | |

(Continued)

FOREIGN PATENT DOCUMENTS

| | | | |
|---|---|---|---|
| AU | 3031677 A | 5/1979 | |
| AU | 517102 B2 | 7/1981 | |

(Continued)

OTHER PUBLICATIONS

AADR. American Association for Dental Research, Summary of Activities, Mar. 20-23, 1980, Los Angeles, CA, p. 195.
(Continued)

*Primary Examiner* — Matthew M Nelson
(74) *Attorney, Agent, or Firm* — Wilson Sonsini Goodrich & Rosati

(57) ABSTRACT

System and methods for positioning 3D virtual brackets on teeth for the precise positioning of conventional brackets and wire. Various reference features may be calculated for the teeth and used to calculate a position for the virtual bracket. Reference features that are calculated include curve of Spee, Andrew's plane, and a facial axis of the clinical crown for the teeth.

21 Claims, 13 Drawing Sheets

Related U.S. Application Data continuation of application No. 11/551,605, filed on Oct. 20, 2006, now Pat. No. 9,326,831.

(56) References Cited

U.S. PATENT DOCUMENTS

| | | |
|---|---|---|
| 3,660,900 A | 5/1972 | Andrews |
| 3,683,502 A | 8/1972 | Wallshein |
| 3,738,005 A | 6/1973 | Cohen et al. |
| 3,860,803 A | 1/1975 | Levine |
| 3,916,526 A | 11/1975 | Schudy |
| 3,922,786 A | 12/1975 | Lavin |
| 3,950,851 A | 4/1976 | Bergersen |
| 3,983,628 A | 10/1976 | Acevedo |
| 4,014,096 A | 3/1977 | Dellinger |
| 4,195,046 A | 3/1980 | Kesling |
| 4,253,828 A | 3/1981 | Coles et al. |
| 4,324,546 A | 4/1982 | Heitlinger et al. |
| 4,324,547 A | 4/1982 | Arcan et al. |
| 4,348,178 A | 9/1982 | Kurz |
| 4,478,580 A | 10/1984 | Barrut |
| 4,500,294 A | 2/1985 | Lewis |
| 4,504,225 A | 3/1985 | Yoshii |
| 4,505,673 A | 3/1985 | Yoshii |
| 4,526,540 A | 7/1985 | Dellinger |
| 4,575,330 A | 3/1986 | Hull |
| 4,575,805 A | 3/1986 | Moermann et al. |
| 4,591,341 A | 5/1986 | Andrews |
| 4,609,349 A | 9/1986 | Cain |
| 4,611,288 A | 9/1986 | Duret et al. |
| 4,656,860 A | 4/1987 | Orthuber et al. |
| 4,663,720 A | 5/1987 | Duret et al. |
| 4,664,626 A | 5/1987 | Kesling |
| 4,676,747 A | 6/1987 | Kesling |
| 4,742,464 A | 5/1988 | Duret et al. |
| 4,755,139 A | 7/1988 | Abbatte et al. |
| 4,763,791 A | 8/1988 | Halverson et al. |
| 4,793,803 A | 12/1988 | Martz |
| 4,798,534 A | 1/1989 | Breads |
| 4,836,778 A | 6/1989 | Baumrind et al. |
| 4,837,732 A | 6/1989 | Brandestini et al. |
| 4,850,864 A | 7/1989 | Diamond |
| 4,850,865 A | 7/1989 | Napolitano |
| 4,856,991 A | 8/1989 | Breads et al. |
| 4,877,398 A | 10/1989 | Kesling |
| 4,880,380 A | 11/1989 | Martz |
| 4,889,238 A | 12/1989 | Batchelor |
| 4,890,608 A | 1/1990 | Steer |
| 4,935,635 A | 6/1990 | O'Harra |
| 4,936,862 A | 6/1990 | Walker et al. |
| 4,937,928 A | 7/1990 | Van Der Zel |
| 4,941,826 A | 7/1990 | Loran et al. |
| 4,964,770 A | 10/1990 | Steinbichler et al. |
| 4,975,052 A | 12/1990 | Spencer et al. |
| 4,983,334 A | 1/1991 | Adell |
| 5,011,405 A | 4/1991 | Lemchen |
| 5,017,133 A | 5/1991 | Miura |
| 5,027,281 A | 6/1991 | Rekow et al. |
| 5,035,613 A | 7/1991 | Breads et al. |
| 5,055,039 A | 10/1991 | Abbatte et al. |
| 5,059,118 A | 10/1991 | Breads et al. |
| 5,100,316 A | 3/1992 | Wildman |
| 5,121,333 A | 6/1992 | Riley et al. |
| 5,125,832 A | 6/1992 | Kesling |
| 5,128,870 A | 7/1992 | Erdman et al. |
| 5,130,064 A | 7/1992 | Smalley et al. |
| 5,131,843 A | 7/1992 | Hilgers et al. |
| 5,131,844 A | 7/1992 | Marinaccio et al. |
| 5,139,419 A | 8/1992 | Andreiko et al. |
| 5,145,364 A | 9/1992 | Martz et al. |
| 5,176,517 A | 1/1993 | Truax |
| 5,184,306 A | 2/1993 | Erdman et al. |
| 5,186,623 A | 2/1993 | Breads et al. |
| 5,257,203 A | 10/1993 | Riley et al. |
| 5,273,429 A | 12/1993 | Rekow et al. |
| 5,278,756 A | 1/1994 | Lemchen et al. |
| 5,328,362 A | 7/1994 | Watson et al. |
| 5,338,198 A | 8/1994 | Wu et al. |
| 5,340,309 A | 8/1994 | Robertson |
| 5,342,202 A | 8/1994 | Deshayes |
| 5,368,478 A | 11/1994 | Andreiko et al. |
| 5,382,164 A | 1/1995 | Stern |
| 5,395,238 A | 3/1995 | Andreiko et al. |
| 5,431,562 A | 7/1995 | Andreiko et al. |
| 5,440,326 A | 8/1995 | Quinn |
| 5,440,496 A | 8/1995 | Andersson et al. |
| 5,447,432 A | 9/1995 | Andreiko et al. |
| 5,452,219 A | 9/1995 | Dehoff et al. |
| 5,454,717 A | 10/1995 | Andreiko et al. |
| 5,456,600 A | 10/1995 | Andreiko et al. |
| 5,474,448 A | 12/1995 | Andreiko et al. |
| RE35,169 E | 3/1996 | Lemchen et al. |
| 5,518,397 A | 5/1996 | Andreiko et al. |
| 5,528,735 A | 6/1996 | Strasnick et al. |
| 5,533,895 A | 7/1996 | Andreiko et al. |
| 5,542,842 A | 8/1996 | Andreiko et al. |
| 5,549,476 A | 8/1996 | Stern |
| 5,562,448 A | 10/1996 | Mushabac |
| 5,587,912 A | 12/1996 | Andersson et al. |
| 5,605,459 A | 2/1997 | Kuroda et al. |
| 5,607,305 A | 3/1997 | Andersson et al. |
| 5,614,075 A | 3/1997 | Andre, Sr. |
| 5,621,648 A | 4/1997 | Crump |
| 5,645,420 A | 7/1997 | Bergersen |
| 5,645,421 A | 7/1997 | Slootsky |
| 5,655,653 A | 8/1997 | Chester |
| 5,683,243 A | 11/1997 | Andreiko et al. |
| 5,692,894 A | 12/1997 | Schwartz et al. |
| 5,725,376 A | 3/1998 | Poirier |
| 5,725,378 A | 3/1998 | Wang |
| 5,733,126 A | 3/1998 | Andersson et al. |
| 5,740,267 A | 4/1998 | Echerer et al. |
| 5,742,700 A | 4/1998 | Yoon et al. |
| 5,799,100 A | 8/1998 | Clarke et al. |
| 5,800,174 A | 9/1998 | Andersson |
| 5,823,778 A | 10/1998 | Schmitt et al. |
| 5,848,115 A | 12/1998 | Little et al. |
| 5,857,853 A | 1/1999 | Van Nifterick et al. |
| 5,866,058 A | 2/1999 | Batchelder et al. |
| 5,879,158 A | 3/1999 | Doyle et al. |
| 5,880,961 A | 3/1999 | Crump |
| 5,880,962 A | 3/1999 | Andersson et al. |
| 5,934,288 A | 8/1999 | Avila et al. |
| 5,957,686 A | 9/1999 | Anthony |
| 5,964,587 A | 10/1999 | Sato |
| 5,971,754 A | 10/1999 | Sondhi et al. |
| 5,975,893 A | 11/1999 | Chishti et al. |
| 6,015,289 A | 1/2000 | Andreiko et al. |
| 6,044,309 A | 3/2000 | Honda |
| 6,049,743 A | 4/2000 | Baba |
| 6,062,861 A | 5/2000 | Andersson |
| 6,068,482 A | 5/2000 | Snow |
| 6,099,314 A | 8/2000 | Kopelman et al. |
| 6,123,544 A | 9/2000 | Cleary |
| 6,152,731 A | 11/2000 | Jordan et al. |
| 6,183,248 B1 | 2/2001 | Chishti et al. |
| 6,190,165 B1 | 2/2001 | Andreiko et al. |
| 6,217,325 B1 | 4/2001 | Chishti et al. |
| 6,217,334 B1 | 4/2001 | Hultgren |
| 6,244,861 B1 | 6/2001 | Andreiko et al. |
| 6,276,932 B1 * | 8/2001 | Jinnouchi ............... A61C 7/02 433/20 |
| 6,309,215 B1 | 10/2001 | Phan et al. |
| 6,315,553 B1 | 11/2001 | Sachdeva et al. |
| 6,322,359 B1 | 11/2001 | Jordan et al. |
| 6,350,120 B1 | 2/2002 | Sachdeva et al. |
| 6,358,044 B1 | 3/2002 | Andreiko |
| 6,382,975 B1 | 5/2002 | Poirier |
| 6,398,548 B1 | 6/2002 | Muhammad et al. |
| 6,402,707 B1 | 6/2002 | Ernst |
| 6,471,511 B1 | 10/2002 | Chishti et al. |
| 6,482,298 B1 | 11/2002 | Bhatnagar |
| 6,514,074 B1 | 2/2003 | Chishti et al. |
| 6,524,101 B1 | 2/2003 | Phan et al. |
| 6,554,611 B2 | 4/2003 | Chishti et al. |

(56) References Cited

U.S. PATENT DOCUMENTS

| | | | |
|---|---|---|---|
| 6,572,372 | B1 | 6/2003 | Phan et al. |
| 6,616,444 | B2 | 9/2003 | Andreiko et al. |
| 6,629,840 | B2 | 10/2003 | Chishti et al. |
| 6,632,089 | B2 * | 10/2003 | Rubbert .................. A61C 7/00 433/24 |
| 6,705,863 | B2 | 3/2004 | Phan et al. |
| 6,712,607 | B2 | 3/2004 | Andreiko |
| 6,722,880 | B2 | 4/2004 | Chishti et al. |
| 6,767,208 | B2 | 7/2004 | Kaza |
| 6,846,179 | B2 | 1/2005 | Chapouland et al. |
| 7,063,532 | B1 | 6/2006 | Jones et al. |
| 7,474,932 | B2 * | 1/2009 | Geng ................ A61C 13/0004 700/98 |
| 7,658,610 | B2 | 2/2010 | Knopp |
| 9,326,831 | B2 | 5/2016 | Cheang |
| 9,844,420 | B2 | 12/2017 | Cheang |
| 10,022,204 | B2 | 7/2018 | Cheang |
| 2002/0006597 | A1 | 1/2002 | Andreiko et al. |
| 2003/0009252 | A1 | 1/2003 | Pavlovskaia et al. |
| 2003/0139834 | A1 | 7/2003 | Nikolskiy et al. |
| 2003/0224311 | A1 | 12/2003 | Cronauer |
| 2004/0128010 | A1 | 7/2004 | Pavlovskaia et al. |
| 2004/0229185 | A1 | 11/2004 | Knopp |
| 2005/0042569 | A1 | 2/2005 | Phan et al. |
| 2005/0055118 | A1 | 3/2005 | Nikolskiy et al. |
| 2005/0064360 | A1 | 3/2005 | Wen et al. |
| 2007/0238064 | A1 * | 10/2007 | Stark ..................... A61C 7/146 433/24 |
| 2008/0096152 | A1 | 4/2008 | Cheang |

FOREIGN PATENT DOCUMENTS

| | | |
|---|---|---|
| AU | 5598894 A | 6/1994 |
| CA | 1121955 A | 4/1982 |
| DE | 2749802 A1 | 5/1978 |
| DE | 69327661 T2 | 7/2000 |
| EP | 0091876 A1 | 10/1983 |
| EP | 0299490 A2 | 1/1989 |
| EP | 0376873 A2 | 7/1990 |
| EP | 0490848 A2 | 6/1992 |
| EP | 0541500 A1 | 5/1993 |
| EP | 0667753 B1 | 1/2000 |
| EP | 0774933 B1 | 12/2000 |
| EP | 0731673 B1 | 5/2001 |
| ES | 463897 A1 | 1/1980 |
| FR | 2369828 A1 | 6/1978 |
| FR | 2652256 A1 | 3/1991 |
| GB | 1550777 A | 8/1979 |
| JP | S5358191 A | 5/1978 |
| JP | H0428359 A | 1/1992 |
| JP | H08508174 A | 9/1996 |
| WO | WO-9104713 A1 | 4/1991 |
| WO | WO-9410935 A1 | 5/1994 |
| WO | WO-9832394 A1 | 7/1998 |
| WO | WO-9844865 A1 | 10/1998 |
| WO | WO-9858596 A1 | 12/1998 |

OTHER PUBLICATIONS

Alcaniz, et aL., "An Advanced System for the Simulation and Planning of Orthodontic Treatments," Karl Heinz Hohne and Ron Kikinis (eds.), Visualization in Biomedical Computing, 4th Intl. Conf., VBC '96, Hamburg, Germany, Sep. 22-25, 1996, Springer-Verlag, pp. 511-520.

Alexander et al., "The DigiGraph Work Station Part 2 Clinical Management," JCO, pp. 402-407 (Jul. 1990).

Altschuler, "3D Mapping of Maxillo-Facial Prosthesis," AADR Abstract #607, 2 pages total, (1980).

Altschuler et al., "Analysis of 3-D Data for Comparative 3-D Serial Growth Pattern Studies of Oral-Facial Structures," IADR Abstracts, Program and Abstracts of Papers, 57th General Session, IADR Annual Session, Mar. 29, 1979-Apr. 1, 1979, New Orleans Marriot, Journal of Dental Research, vol. 58, Jan. 1979, Special Issue A, p. 221.

Altschuler et al., "Laser Electro-Optic System for Rapid Three-Dimensional (3D) Topographic Mapping of Surfaces," Optical Engineering, 20(6):953-961 (1981).

Altschuler et al., "Measuring Surfaces Space-Coded by a Laser-Projected Dot Matrix," SPIE Imaging Applications for Automated Industrial Inspection and Assembly, vol. 182, p. 187-191 (1979).

Andersson et al., "Clinical Results with Titanium Crowns Fabricated with Machine Duplication and Spark Erosion," Acta. Odontol. Scand., 47:279-286 (1989).

Andrews, The Six Keys to Optimal Occlusion Straight Wire, Chapter 3, pp. 13-24 (1989).

Bartels, et al., An Introduction to Splines for Use in Computer Graphics and Geometric Modeling, Morgan Kaufmann Publishers, pp. 422-425 (1987).

Baumrind, "A System for Craniofacial Mapping Through the Integration of Data from Stereo X-Ray Films and Stereo Photographs," an invited paper submitted to the 1975 American Society of Photogram Symposium on Close-Range Photogram Systems, University of III., Aug. 26-30, 1975, pp. 142-166.

Baumrind et al., "A Stereophotogrammetric System for the Detection of Prosthesis Loosening in Total Hip Arthroplasty," NATO Symposium on Applications of Human Biostereometrics, Jul. 9-13, 1978, SPIE, vol. 166, pp. 112-123.

Baumrind et al., "Mapping the Skull in 3-D," reprinted from J. Calif. Dent. Assoc., 48(2), 11 pages total, (1972 Fall Issue).

Baumrind, "Integrated Three-Dimensional Craniofacial Mapping: Background, Principles, and Perspectives," Semin. In Orthod., 7(4):223-232 (Dec. 2001).

Begole et al., "A Computer System for the Analysis of Dental Casts," The Angle Orthod., 51(3):253-259 (Jul. 1981).

Bernard et al., "Computerized Diagnosis in Orthodontics for Epidemiological Studies: A Progress Report," Abstract, J. Dental Res. Special Issue, vol. 67, p. 169, paper presented at International Association for Dental Research 66th General Session, Mar. 9-13, 1988, Montreal, Canada.

Bhatia et al., "A Computer-Aided Design for Orthognathic Surgery," Br. J. Oral Maxillofac. Surg., 22:237-253 (1984).

Biggerstaff, "Computerized Diagnostic Setups and Simulations," Angle Orthod., 40(1):28-36 (Jan. 1970).

Biggerstaff et al., "Computerized Analysis of Occlusion in the Postcanine Dentition," Am. J. Orthod., 61(3): 245-254 (Mar. 1972).

Biostar Opeation & Training Manual. Great Lakes Orthodontics, Ltd. 199 Fire Tower Drive, Tonawanda, New York. 14150-5890, 20 pages total (1990).

Blu, et al., "Linear interpolation revitalized", IEEE Trans. Image Proc., 13(5):710-719 (May 2004.

Bourke, "Coordinate System Transformation," (Jun. 1996), p. 1, retrieved from the Internet Nov. 5, 2004, URL< http://astronomy.swin.edu.au/—pbourke/prolection/coords>.

Boyd et al., "Three Dimensional Diagnosis and Orthodontic Treatment of Complex Malocclusions with the Invisalipn Appliance," Semin. Orthod., 7(4):274-293 (Dec. 2001).

Brandestini et al., "Computer Machined Ceramic Inlays: In Vitro Marginal Adaptation," J. Dent. Res. Special Issue, Abstract 305, vol. 64, p. 208 (1985).

Brook et al., "An Image Analysis System for the Determination of Tooth Dimensions from Study Casts: Comparison with Manual Measurements of Mesio-distal Diameter," J. Dent. Res., 65(3):428-431 (Mar. 1986).

Burstone et al., Precision Adjustment of the Transpalatal Lingual Arch: Computer Arch Form IN Predetermination, Am, Journal of Orthodontics, vol. 79, No. 2 (Feb. 1981), pp. 115-133.

Burstone (interview), "Dr. Charles J. Burstone on the Uses of the Computer in Orthodontic Practice (Part 1)," J. Clin. Orthod., 13(7):442-453 (Jul. 1979).

Burstone (interview), "Dr. Charles J. Burstone on the Uses of the Computer in Orthodontic Practice (Part 2)," J. Clin. Orthod., 13(8):539-551 (Aug. 1979).

Cardinal Industrial Finishes, Powder Coatings information posted at<http://www.cardinalpaint.com> on Aug. 25, 2000, 2 pages.

(56) References Cited

OTHER PUBLICATIONS

Carnaghan, "An Alternative to Holograms for the Portrayal of Human Teeth," 4th Int'l. Conf. on Holographic Systems, Components and Applications, Sep. 15, 1993, pp. 228-231.

Chaconas et al., "The DigiGraph Work Station, Part 1, Basic Concepts," JCO, pp. 360-367 (Jun. 1990).

Chafetz et al., "Subsidence of the Femoral Prosthesis, A Stereophotogrammetric Evaluation," Clin. Orthop. Relat. Res., No. 201, pp. 60-67 (Dec. 1985).

Chiappone, (1980). Constructing the Gnathologic Setup and Positioner, J. Clin. Orthod, vol. 14, pp. 121-133.

Cottingham, (1969). Gnathologic Clear Plastic Positioner, Am. J. Orthod, vol. 55, pp. 23-31.

Crawford, "CAD/CAM in the Dental Office: Does It Work?", Canadian Dental Journal, vol. 57, No. 2, pp. 121-123 (Feb. 1991).

Crawford, "Computers in Dentistry: Part 1 CAD/CAM: The Computer Moves Chairside," Part 2 F. Duret—A Man with a Vision, "Part 3 the Computer Gives New Vision—Literally," Part 4 Bytes 'N Bites—The Computer Moves from the Front Desk to the Operatory, Canadian Dental Journal, vol. 54 (9), pp. 661-666 (1988).

Crooks, "CAD/CAM Comes to USC," USC Dentistry, pp. 14-17 (Spring 1990).

Cureton, Correcting Malaligned Mandibular Incisors with Removable Retainers, J. Clin. Orthod, vol. 30, No. 7 (1996) pp. 390-395.

Curry et al., "Integrated Three-Dimensional Craniofacial Mapping at the Craniofacial Research Instrumentation Laboratory/University of the Pacific," Semin. Orthod., 7(4):258-265 (Dec. 2001).

Cutting et a/., "Three-Dimensional Computer-Assisted Design of Craniofacial Surgical Procedures: Optimization and Interaction with Cephalometric and CT-Based Models," Plast. 77(6):877-885 (Jun. 1986).

DCS Dental AG, "The CAD/CAM 'DCS Titan System' for Production of Crowns/Bridges," DSC Production AG, pp. 1-7 (Jan. 1992.

Definition for gingiva. Dictionary.com p. 1-3. Retrieved from the internet Nov. 5, 2004<http://reference.com/search/search?q=gingiva>.

Defranco et al., "Three-Dimensional Large Displacement Analysis of Orthodontic Appliances," J. Biomechanics, 9:793-801 (1976).

Dental Institute University of Zurich Switzerland, Program for International Symposium JD on Computer Restorations: State of the Art of the CEREC-Method, May 1991, 2 pages total.

Dentrac Corporation, Dentrac document, pp. 4-13 (1992).

DENT-X posted on Sep. 24, 1998 at< http://www.dent-x.com/DentSim.htm>, 6 pages.

Doyle, "Digital Dentistry," Computer Graphics World, pp. 50-52, 54 (Oct. 2000).

DuraClearTM product information, Allesee Orthodontic Appliances-Pro Lab, 1 page (1997).

Duret et al., "CAD/CAM Imaging in Dentistry," Curr. Opin. Dent., 1:150-154 (1991).

Duret et al, "CAD-CAM in Dentistry," J. Am. Dent. Assoc. 117:715-720 (Nov. 1988).

Duret, "The Dental CAD/CAM, General Description of the Project," Hennson International Product Brochure, 18 pages total, Jan. 1986.

Duret, "Vers Une Prosthese Informatisee," (English translation attached), Tonus, vol. 75, pp. 55-57 (Nov. 15, 1985).

Economides, "The Microcomputer in the Orthodontic Office," JCO, pp. 767-772 (Nov. 1979).

Elsasser, Some Observations on the History and Uses of the Kesling Positioner, Am. J. Orthod. (1950) 36:368-374.

English translation of Japanese Laid-Open Publication No. 63-11148 to inventor T. Ozukuri (Laid-Open on Jan. 18, 1998) pp. 1-7.

Felton et al., "A Computerized Analysis of the Shape and Stability of Mandibular Arch Form," Am. J. Orthod. Dentofacial Orthop., 92(6):478-483 (Dec. 1987).

Friede et al., "Accuracy of Cephalometric Prediction in Orthognathic Surgery," Abstract of Papers, J. Dent. Res., 70:754-760 (1987).

Futterling et a/., "Automated Finite Element Modeling of a Human Mandible with Dental Implants," JS WSCG '98-Conference Program, retrieved from the Internet<http://wscg.zcu.cz/wscg98/papers98/Strasser 98.pdf>, 8 pages.

Gao et al., "3-D element Generation for Multi-Connected Complex Dental and Mandibular Structure," Proc. Intl Workshop on Medical Imaging and Augmented Reality, pp. 267-271 (Jun. 12, 2001).

Gim-Alldent Deutschland, "Das DUX System: Die Technik," 2 pages total (2002).

Gottleib et al., "JCO Interviews Dr. James A. McNamura, Jr., on the Frankel Appliance: Part 2: Clinical 1-1 Management," J. Clin. Orthod., 16(6):390-407 (Jun. 1982).

Grayson, "New Methods for Three Dimensional Analysis of Craniofacial Deformity, Symposium: JW Computerized Facial Imaging in Oral and Maxiiofacial Surgery," AAOMS, 3 pages total, (Sep. 13, 1990).

Guess et al., "Computer Treatment Estimates in Orthodontics and Orthognathic Surgery," JCO, pp. 262-228 (Apr. 1989).

Heaven et a/., "Computer-Based Image Analysis of Artificial Root Surface Caries," Abstracts of Papers, J. Dent. Res., 70:528 (Apr. 17-21, 1991).

Highbeam Research, "Simulating Stress Put on Jaw," Tooling & Production [online], Nov. 1996, n pp. 1-2, retrieved from the Internet on Nov. 5, 2004, URL http://static.highbeam.com/t/toolingampproduction/november011996/simulatingstressput-onfa . . . >.

Hikage, "Integrated Orthodontic Management System for Virtual Three-Dimensional Computer Graphic Simulation and Optical Video Image Database for Diagnosis and Treatment Planning", Journal of Japan KA Orthodontic Society, Feb. 1987, English translation, pp. 1-38, Japanese version, 46(2), pp. 248-269 (60 pages total).

Hoffmann, et al., "Role of Cephalometry for Planning of Jaw Orthopedics and Jaw Surgery Procedures," (Article Summary in English, article in German), Informatbnen, pp. 375-396 (Mar. 1991).

Hojjatie et al., "Three-Dimensional Finite Element Analysis of Glass-Ceramic Dental Crowns," J. Biomech., 23(11):1157-1166 (1990).

Huckins, "CAD-CAM Generated Mandibular Model Prototype from MRI Data," AAOMS, p. 96 (1999).

Important Tip About Wearing the Red White & Blue Active Clear Retainer System, Allesee Orthodontic Appliances-Pro Lab, 1 page 1998).

JCO Interviews, Craig Andreiko , DDS, MS on the Elan and Orthos Systems, JCO, pp. 459-468 (Aug. 1994).

JCO Interviews, Dr. Homer W. Phillips on Computers in Orthodontic Practice, Part 2, JCO. 1997; 1983:819-831.

Jerrold, "The Problem, Electronic Data Transmission and the Law," AJO-DO, pp. 478-479 (Apr. 1988).

Jones et al., "An Assessment of the Fit of a Parabolic Curve to Pre- and Post-Treatment Dental Arches," Br. J. Orthod., 16:85-93 (1989).

JP Faber et al., "Computerized Interactive Orthodontic Treatment Planning," Am. J. Orthod., 73(1):36-46 (Jan. 1978).

Kamada et.al., Case Reports on Tooth Positioners Using LTV Vinyl Silicone Rubber, J. Nihon University School of Dentistry (1984) 26(1): 11-29.

Kamada et.al., Construction of Tooth Positioners with LTV Vinyl Silicone Rubber and Some Case KJ Reports, J. Nihon University School of Dentistry (1982) 24(1):1-27.

Kanazawa et al., "Three-Dimensional Measurements of the Occlusal Surfaces of Upper Molars in a Dutch Population," J. Dent Res., 63(11):1298-1301 (Nov. 1984).

Kesling, Coordinating the Predetermined Pattern and Tooth Positioner with Conventional Treatment, KN Am. J. Orthod. Oral Surg. (1946) 32:285-293.

Kesling et al., The Philosophy of the Tooth Positioning Appliance, American Journal of Orthodontics and Oral surgery. 1945; 31:297-304.

Kleeman et al., The Speed Positioner, J. Clin. Orthod. (1996) 30:673-680.

Kochanek, "Interpolating Splines with Local Tension, Continuity and Bias Control," Computer Graphics, ri 18(3):33-41 (Jul. 1984).

KM Oral Surgery (1945) 31 :297-30.

(56) References Cited

OTHER PUBLICATIONS

Kunii et al., "Articulation Simulation for an Intelligent Dental Care System," Displays 15:181-188 (1994).
Kuroda et al., Three-Dimensional Dental Cast Analyzing System Using Laser Scanning, Am. J. Orthod. Dentofac. Orthop. (1996) 110:365-369.
Laurendeau, et al., "A Computer-Vision Technique for the Acquisition and Processing of 3-D Profiles of 7 KR Dental Imprints: An Application in Orthodontics," IEEE Transactions on Medical Imaging, 10(3):453-461 (Sep. 1991).
Leinfelder, et al., "A New Method for Generating Ceramic Restorations: a CAD-CAM System," J. Am. 1-1 Dent. Assoc., 118(6):703-707 (Jun. 1989).
Manetti, et al., "Computer-Aided Cefalometry and New Mechanics in Orthodontics," (Article Summary in English, article in German), Fortschr Kieferorthop. 44, 370-376 (Nr. 5), 1983.
McCann, "Inside the ADA," J. Amer. Dent. Assoc., 118:286-294 (Mar. 1989).
McNamara et al., "Invisible Retainers," J. Cfin. Orthod., pp. 570-578 (Aug. 1985).
McNamara et al., Orthodontic and Orthopedic Treatment in the Mixed Dentition, Needham Press, pp. 347-353 (Jan. 1993).
Moermann et al., "Computer Machined Adhesive Porcelain Inlays: Margin Adaptation after Fatigue Stress," IADR Abstract 339, J. Dent. Res., 66(a):763 (1987).
Moles, "Correcting Mild Malalignments—As Easy As One, Two, Three," AOA/Pro Corner, vol. 11, No. 1, 2 pages (2002).
Mormann et al., "Marginale Adaptation von adhasuven Porzellaninlays in vitro," Separatdruck aus: Schweiz. Mschr. Zahnmed. 95: 1118-1129, 1985.
Nahoum, "The Vacuum Formed Dental Contour Appliance," N. Y. State Dent. J., 30(9):385-390 (Nov. 1964).
Nash, "CEREC CAD/CAM Inlays: Aesthetics and Durability in a Single Appointment," Dent. Today, 9(8):20, 22-23 (Oct. 1990).
Nishiyama et al., "A New Construction of Tooth Repositioner by LTV Vinyl Silicone Rubber," J. Nihon Univ. Sch. Dent., 19(2):93-102 (1977).
Paul et al., "Digital Documentation of Individual Human Jaw and Tooth Forms for Applications in Orthodontics, Oral Surgery and Forensic Medicine" Proc. of the 24th Annual Conf. of the IEEE Industrial Electronics Society (IECON '98), Sep. 4, 1998, pp. 2415-2418.
Pinkham, "Foolish Concept Propels Technology," Dentist, 3 pages total, Jan./Feb. 1989.
Pinkham, "Inventors CAD/CAM May Transform Dentistry," Dentist, 3 pages total, Sep. 1990.
Ponitz, "Invisible Retainers," Am. J. Orthod., 59(3):266-272 (Mar. 1971).
PROCERA Research Projects, "PROCERA Research Projects 1993—Abstract Collection," pp. 3-7; 28 (1993).
Proffit et al., Contemporary Orthodontics, (Second Ed.), Chapter 15, Mosby Inc., pp. 470-533 (Oct. 1993.
Raintree Essix & ARS Materials, Inc., Raintree Essix, Technical Magazine Table of contents and Essix Appliances,< http:// www.essix.com/magazine/defaulthtml> Aug. 13, 1997.
Redmond et al., "Clinical Implications of Digital Orthodontics," Am. J. Orthod. Dentofacial Orthop., 117(2):240-242 (2000).
Rekow, "A Review of the Developments in Dental CAD/CAM Systems," (contains references to Japanese efforts and content of the papers of particular interest to the clinician are indicated with a one line summary of their content in the bibliography), Curr. Opin. Dent., 2:25-33 (Jun. 1992).
Rekow, "CAD/CAM in Dentistry: A Historical Perspective and View of the Future," J. Can. Dent. Assoc., 58(4):283, 287-288 (Apr. 1992).
Rekow, "Computer-Aided Design and Manufacturing in Dentistry: A Review of the State of the Art," J. Prosthet. Dent., 58(4):512-516 (Oct. 1987).
Rekow, "Dental CAD-CAM Systems: What is the State of the Art?", J. Amer. Dent. Assoc., 122:43-48 1991.
Rekow et al., "CAD/CAM for Dental Restorations—Some of the Curious Challenges," IEEE Trans. Biomed. Eng., 38(4):314-318 (Apr. 1991).
Rekow et al., "Comparison of Three Data Acquisition Techniques for 3-D Tooth Surface Mapping," Annual International Conference of the IEEE Engineering in Medicine and Biology Society, 13(1):344-345 1991.
Rekow, "Feasibility of an Automated System for Production of Dental Restorations, Ph.D. Thesis," Univ. of Minnesota, 244 pages total, Nov. 1988.
Richmond et al., "The Development of a 3D Cast Analysis System," Br. J. Orthod., 13(1):53-54 (Jan. 1986).
Richmond et al., "The Development of the PAR Index (Peer Assessment Rating): Reliability and Validity," Eur. J. Orthod., 14:125-139 (1992).
Richmond, "Recording the Dental Cast in Three Dimensions," Am. J. Orthod. Dentofacial Orthop., 92(3):199-206 (Sep. 1987).
Rudge, "Dental Arch Analysis: Arch Form, A Review of the Literature," Eur. J. Orthod., 3(4):279-284 1981.
Sakuda et al., "Integrated Information-Processing System in Clinical Orthodontics: An Approach with Use of a Computer Network System," Am. J. Orthod. Dentofacial Orthop., 101(3): 210-220 (Mar. 1992).
Schellhas et al., "Three-Dimensional Computed Tomography in Maxillofacial Surgical Planning," Arch. Otolamp!. Head Neck Sur9., 114:438-442 (Apr. 1988).
Schroeder et al., Eds. The Visual Toolkit, Prentice Hall PTR, New Jersey (1998) Chapters 6, 8 & 9, (pp. 153-210,309-354, and 355-428, respectively.
Shilliday, (1971). Minimizing finishing problems with the minipositioner, Am. J. Orthod. 59:596-599.
Siemens, "CEREC—Computer-Reconstruction," High Tech in der Zahnmedizin, 14 pages total (2004).
Sinclair, "The Readers' Corner," J. Clin. Orthod., 26(6):369-372 (Jun. 1992).
Sirona Dental Systems GmbH, CEREC 3D, Manuel utiiisateur, Version 2.0X (in French), 2003,114 pages total.
Stoll et al., "Computer-aided Technologies in Dentistry," (article summary in English, article in German), Dtsch Zahna'rztl Z 45, pp. 314-322 (1990).
Sturman, "Interactive Keyframe Animation of 3-D Articulated Models," Proceedings Graphics Interface '84, May-Jun. 1984, pp. 35-40.
The Choice is Clear: Red, White & Blue . . . The Simple, Affordable, No-Braces Treatment, Allesee HI Orthodontic Appliances-Pro Lab product information for doctors. http://ormco.com/aoa/appliancesservices/RWB/doctorhtml>, 5 pages (May 19, 2003).
The Choice is Clear: Red, White & Blue . . . The Simple, Affordable, No-Braces Treatment, Allesee HJ Orthodontic Appliances-Pro Lab product information for patients,<http://ormco.com/aoa/appliancesservices/Rwb/patients.html>, 2 pages (May 19, 2003).
The Choice is Clear: Red, White & Blue . . . The Simple, Affordable, No-Braces Treatment, Allesee Orthodontic Appliances-Pro Lab product information, 6 pages (2003).
The Red, White & Blue Way to Improve Your Smile! Allesee Orthodontic Appliances-Pro Lab product information for patients, 2 pages 1992.
Truax L., "Truax Clasp-Less(TM) Appliance System," Funct. Orthod., 9(5):22-4, 26-8 (Sep.-Oct. 1992).
Tru-Tain Orthodontic & Dental Supplies, Product Brochure, Rochester, Minnesota 55902, 16 pages total (1996).
U.S. Department of Commerce, National Technical Information Service, "Automated Crown Replication Using Solid Photography SM," Solid Photography Inc., Melville NY, Oct. 1977, 20 pages total.
U.S. Department of Commerce, National Technical Information Service, "Holodontography: An Introduction to Dental Laser Holography," School of Aerospace Medicine Brooks AFB Tex, Mar. 1973, 37 pages total.
U.S. Appl. No. 60/050,342, filed Jun. 20, 1997, 41 pages total.
Van Der Linden, "A New Method to Determine Tooth Positions and Dental Arch Dimensions," J. Dent. Res., 51(4):1104 (Jul.-Aug. 1972).

(56) References Cited

OTHER PUBLICATIONS

Van Der Linden et al., "Three-Dimensional Analysis of Dental Casts by Means of the Optocom," J. Dent. Res., p. 1100 (Jul.-Aug. 1972).

Van Der Zel, "Ceramic-Fused-to-Metal Restorations with a New CAD/CAM System," Quintessence Int., 24(11):769-778 (1993.

Varady et al., "Reverse Engineering of Geometric Models—An Introduction," Computer-Aided Design, 29(4):255-268,1997.

Verstreken et al., "An Image-Guided Planning System for Endosseous Oral Implants," IEEE Trans. Med. Imaging, 17(5):842-852 (Oct. 1998).

Warunek et al., Physical and Mechanical Properties of Elastomers in Orthodonic Positioners, Am J. Orthod. Dentofac. Orthop, vol. 95, No. 5, (May 1989) pp. 399-400.

Warunek et.al., Clinical Use of Silicone Elastomer Applicances, JCO (1989) XXIII(10):694-700.

Wells, Application of the Positioner Appliance in Orthodontic Treatment, Am. J. Orthodont. (1970) 58:351-366.

Williams, "Dentistry and CAD/CAM: Another French Revolution," J. Dent. Practice Admin., pp. 2-5 (Jan./Mar. 1987).

Williams, "The Switzerland and Minnesota Developments in CAD/CAM," J. Dent. Practice Admin., pp. 50-55 (Apr./Jun. 1987.

Wishan, "New Advances in Personal Computer Applications for Cephalometric Analysis, Growth Prediction, Surgical Treatment Planning and Imaging Processing," Symposium: Computerized Facial Imaging in Oral and Maxilofacial Surgery Presented on Sep. 13, 1990.

WSCG'98—Conference Program, "The Sixth International Conference in Central Europe on Computer Graphics and Visualization '98," Feb. 9-13, 1998, pp. 1-7, retrieved from the Internet on Nov. 5, 2004, URL<http://wscg.zcu.cz/wscg98/wscg98.h>.

Xia et al., "Three-Dimensional Virtual-Reality Surgical Planning and Soft-Tissue Prediction for Orthognathic Surgery," IEEE Trans. Inf. Technol. Biomed., 5(2):97-107 (Jun. 2001).

Yamamoto et al., "Optical Measurement of Dental Cast Profile and Application to Analysis of Three-Dimensional Tooth Movement in Orthodontics," Front. Med. Biol. Eng., 1(2):119-130 (1988).

Yamamoto et al., "Three-Dimensional Measurement of Dental Cast Profiles and Its Applications to Orthodontics," Conf. Proc. IEEE Eng. Med. Biol. Soc., 12(5):2051-2053 (1990).

Yamany et al., "A System for Human Jaw Modeling Using Intra-Oral Images," Proc. of the 20th Annual Conf. of the IEEE Engineering in Medicine and Biology Society, Nov. 1, 1998, vol. 2, pp. 563-566.

Yoshii, "Research on a New Orthodontic Appliance: The Dynamic Positioner (D.P.); I. The D.P. Concept and Implementation of Transparent Silicone Resin (Orthocon)," Nippon Dental Review, 452:61-74 (Jun. 1980).

Yoshii, "Research on a New Orthodontic Appliance: The Dynamic Positioner (D.P.); II. The D.P. Manufacturing Procedure and Clinical Applications," Nippon Dental Review, 454:107-130 (Aug. 1980).

Yoshii, "Research on a New Orthodontic Appliance: The Dynamic Positioner (D.P.); III. The General Concept of the D.P. Method and Its Therapeutic Effect, Part 1, Dental and Functional Reversed Occlusion Case Reports," Nippon Dental Review, 457:146-164 (Nov. 1980).

Yoshii, "Research on a New Orthodontic Appliance: The Dynamic Positioner (D.P.); II.—The General Concept of the D.P. Method and Its Therapeutic Effect, Part 2. Skeletal Reversed Occlusion Case Reports," Nippon Dental Review, 458:112-129 (Dec. 1980).

You May Be a Candidate for This Invisible No-Braces Treatment, Allesee Orthodontic Appliances-Pro Lab product information for patients, 2 pages (2002).

* cited by examiner

SYSTEM AND METHOD FOR POSITIONING THREE-DIMENSIONAL BRACKETS ON TEETH

CROSS-REFERENCE

This application is a continuation of U.S. patent application Ser. No. 15/842,246, filed Dec. 14, 2017, now U.S. Pat. No. 10,022,204, issued Jul. 17, 2018, which is a continuation of U.S. patent application Ser. No. 14/991,827, filed Jan. 8, 2016, now U.S. Pat. No. 9,844,420, issued Dec. 19, 2017, which is a continuation of U.S. patent application Ser. No. 11/551,605, filed Oct. 20, 2006, now U.S. Pat. No. 9,326,831, issued May 3, 2016, the entire disclosures of which are incorporated herein by reference.

FIELD OF INVENTION

The present invention relates generally to the field of orthodontics, and in particular, to system and method for positioning of three-dimensional brackets on teeth.

BACKGROUND OF THE INVENTION

One objective of orthodontics is to move a patient's teeth to positions where the teeth function optimally and are also aesthetically pleasing. Conventional appliances such as braces and wires are applied to the teeth of a patient by an orthodontist. Once mounted on the teeth, the braces exert continual force on the teeth and gradually urge the teeth to their respective ideal position. The orthodontist does this by adjusting the braces over time to move the teeth toward their final destination.

Orthodontic brackets are often bonded directly to the patient's teeth. Typically, a small quantity of adhesive is placed on the base of each bracket and the bracket is then placed on a selected tooth. Before the adhesive is set, the bracket is maneuvered to a desired location on the tooth. Once the adhesive has hardened, the bracket is bonded to the tooth with sufficient strength to withstand subsequent orthodontic forces as treatment progresses. One shortcoming with this technique is the difficulty in accessing the optimal surface for bracket placement on severely crowded teeth or in teeth where the bonding surface is obstructed by teeth in the opposing arch during jaw closure. With posterior teeth, the treatment provider may have difficulty seeing the precise position of the bracket relative to the tooth surface. The amount of time needed to carry out the bonding procedure may be a nuisance both to the patient as well as to the treatment provider. Also, the necessity of minimizing moisture contamination from the patient's saliva can prolong the procedure and also unduly impair the accuracy of placement of the brackets on the teeth. All of these factors increase the chance that one or more brackets will be incorrectly positioned on the teeth.

Apparatus, systems, and methods have been developed to facilitate teeth movement utilizing clear, removable teeth aligners as an alternative to braces. A mold of the patient's bite is initially taken and desired ending positions for the patient's teeth (i.e., a functionally and aesthetically optimum position) are determined, based on a prescription provided by an orthodontist or dentist. Corrective paths between the initial positions of the teeth and their desired ending positions are then planned. These corrective paths generally include a plurality of intermediate positions between the initial and ending positions of the teeth. Multiple clear, removable aligners formed to move the teeth to the various positions along the corrective path are then manufactured. One system for providing such aligners is the Invisalign® System from Align Technologies, Inc. of Santa Clara, Calif.

Since each patient is unique and requires customized treatment, on occasion, a patient may need to utilize a combination of braces/wires and aligners. Alternatively, after planning a series of aligners for a patient, it may be desired to treat the patient with the conventional bracket and wire approach. Ideally, a system would enable precise placement of brackets on teeth with minimal risk of displacing the brackets upon removal of the matrix and allow final placement to be independent of adjacent geometries.

SUMMARY OF THE INVENTION

Systems and methods for positioning brackets on teeth, such as virtual 3D brackets on teeth in a virtual 3D jaw pair model, are disclosed. In accordance with an exemplary embodiment, a computer-implemented system calculates reference features, determines an initial placement of the virtual brackets using the reference features, allows the user to modify the placement of the virtual brackets, and fabricates a dental template to locate the brackets on the patient's teeth.

BRIEF DESCRIPTION OF THE DRAWINGS

A more complete understanding of the present invention may be derived by referring to the detailed description and claims when considered in connection with the drawing Figures, where like reference numbers refer to similar elements throughout the Figures, and:

DETAILED DESCRIPTION OF THE INVENTION

The present invention may be described herein in terms of various components and processing steps. It should be appreciated that such components and steps may be realized by any number of hardware and software components configured to perform the specified functions. For example, the present invention may employ various electronic control devices, visual display devices, input terminals and the like, which may carry out a variety of functions under the control of one or more control systems, microprocessors or other control devices. In addition, the present invention may be practiced in any number of orthodontic contexts and the exemplary embodiments relating to a system and method for positioning virtual brackets on teeth in a virtual 3D jaw pair model as described herein are merely a few of the exemplary applications for the invention. For example, the principles, features and methods discussed may be applied to any orthodontic treatment application.

U.S. patent application Ser. Nos. 09/264,547 and 09/311,716, now U.S. Pat. No. 6,514,074 describe techniques for generating 3-dimensional digital data sets containing models of individual components of a patient's dentition. These data sets include digital models of individual teeth and the gingival tissue surrounding the teeth. Furthermore, these applications also describe computer-implemented techniques for using the digital models in designing and simulating an orthodontic treatment plan for the patient. For example, one such technique involves receiving an initial data set that represents the patient's teeth before treatment, specifying a desired arrangement of the patient's teeth after treatment, and calculating transformations that will move the teeth from the initial to the final positions over desired treatment paths. U.S. patent application Ser. No. 09/1169,276 also describes the creation of data sets representing the tooth positions at various treatment stages and the use of these data sets to produce orthodontic appliances that implement the treatment plan. One technique for producing an orthodontic appliance involves creating a positive mold of the patient's dentition at one of the treatment stages and using a conventional pressure molding technique to form the appliance around the positive mold. A design of orthodontic appliances from the digital dentition models is, for example, described in U.S. patent application Ser. No. 09/169,034.

Figure 1A:
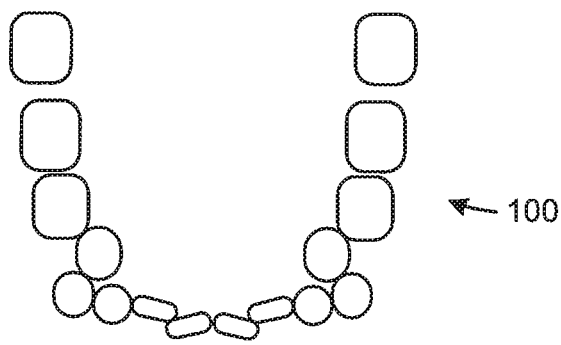
FIGS. 1A, 1B, and 1C illustrate diagrams showing the arrangement of a patient's teeth at an initial stage, an intermediate stage, and a final stage, respectively, of orthodontic treatment.
Figure 1B:
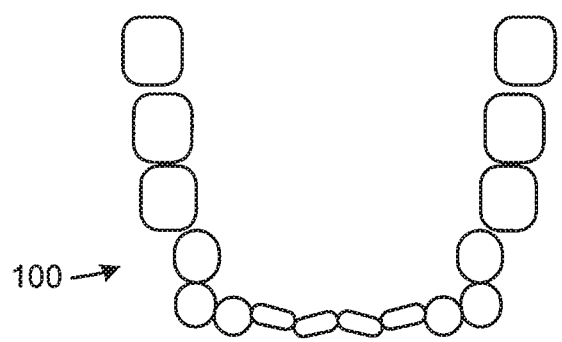
Figure 1C:
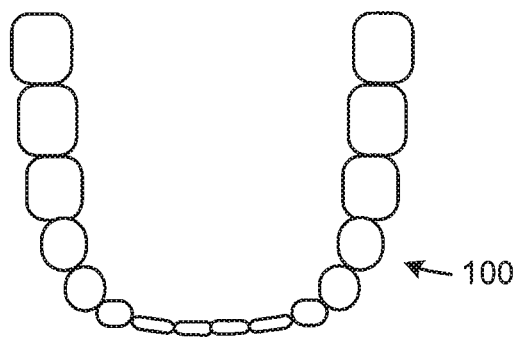

FIGS. 1A, 1B, and 1C illustrate a patient's dentition at three stages during a course of treatment. FIG. 1A illustrates the initial positions of the patient's teeth before treatment begins. A digital model of the teeth at these initial positions is captured in an initial digital data set (IDDS).

Such an IDDS may be obtained in a variety of ways. For example, the patient's teeth may be scanned or imaged using well known technology, such as X-rays, three-dimensional x-rays, computer-aided tomographic images or data sets, magnetic resonance images, and the like.

Methods for digitizing such conventional images to produce data sets are well known and described in the patent and medical literature. By way of example, one approach is to first obtain a plaster cast of the patient's teeth by well known techniques, such as those described in Graber, Orthodontics: Principle and Practice, Second Edition, Saunders, Pa., 1969, pp. 401-415. After the tooth casting is obtained, it can be digitally scanned using a conventional laser scanner or other range acquisition system to produce the IDDS. The data set produced by the range acquisition system may, of course, be converted to other formats to be compatible with the software which is used for manipulating images within the data set. General techniques for producing plaster casts of teeth and generating digital models using laser scanning techniques are described, for example, in U.S. Pat. No. 5,605,459. In accordance with another exemplary embodiment, the acquiring of a digital model of a patient's teeth can also comprise such techniques as disclosed in U.S. Pat. No. 6,767,208, entitled "System and Method for Positioning Teeth", assigned to Align Technology, Inc. Accordingly, any methodology or process for converting scanned data into a digital representation or otherwise for the acquiring of a digital model of a patient's teeth can be utilized.

FIG. 1B illustrates an example of how the patient's teeth may be oriented at an intermediate stage in the treatment process, and FIG. 1C illustrates an example of how the patient's teeth may be oriented at their final positions. A human operator and/or a computer program manipulate the digital models of the patient's teeth to prescribe the final tooth positions. The program then calculates one or more of the intermediate positions, taking into account any constraints imposed on the movement of the teeth by the human operator or by the natural characteristics of the teeth themselves. The program also accounts for any collisions that might occur between teeth as the teeth move from one treatment stage to the next. Selecting the final and intermediate tooth positions and the treatment paths along which the teeth move is described in more detail in one or more of the Patent Applications discussed above, which are all hereby incorporated by reference, in their respective entireties.

Figure 1D:
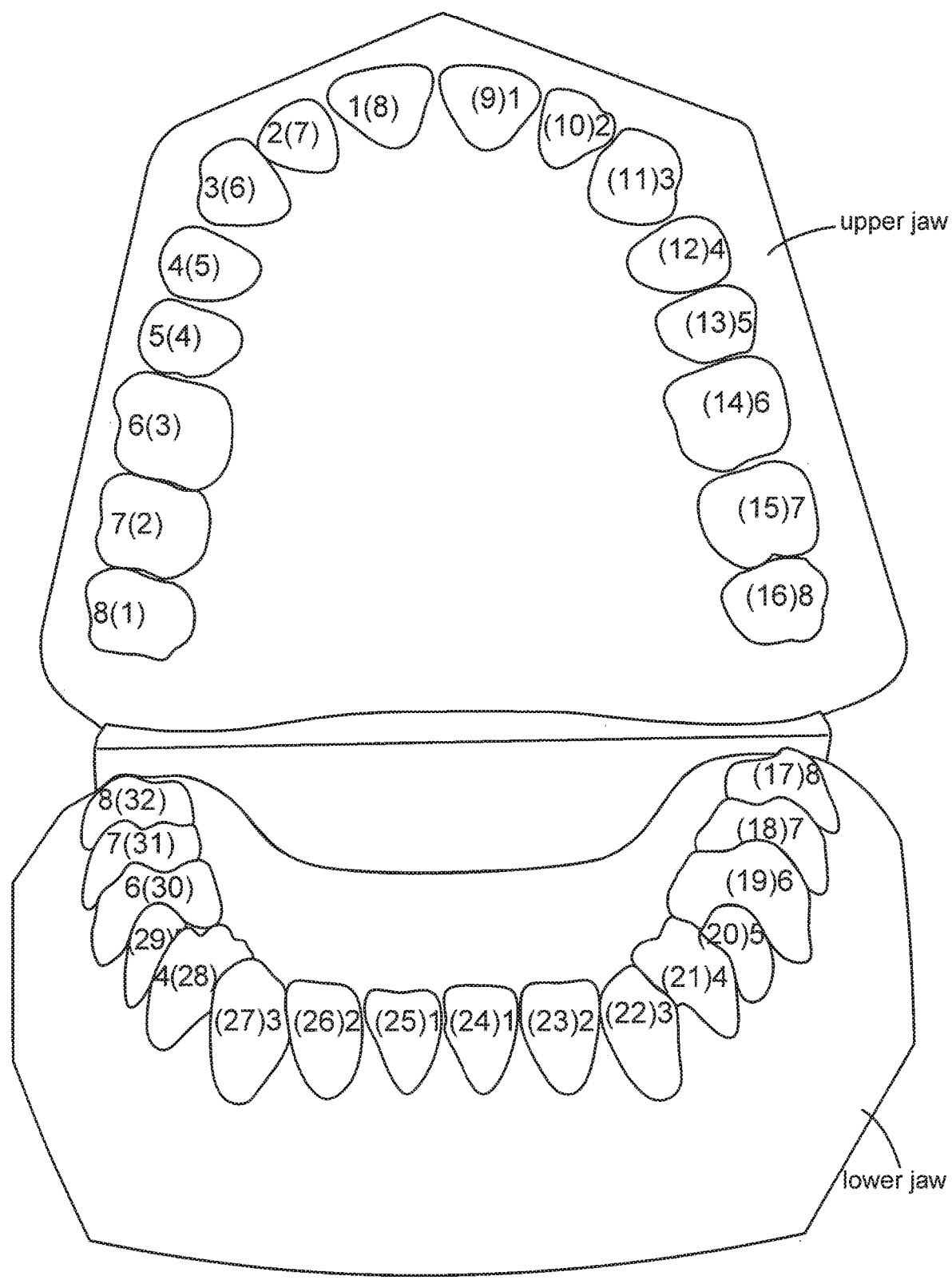
FIG. 1D illustrates a diagram showing teeth numbering according to the standard system of tooth numbering.

FIG. 1D is a diagram of a set of teeth showing the standard system of numbering teeth. Reference is made to this standard system of numbering throughout the discussion below.

Figure 2:
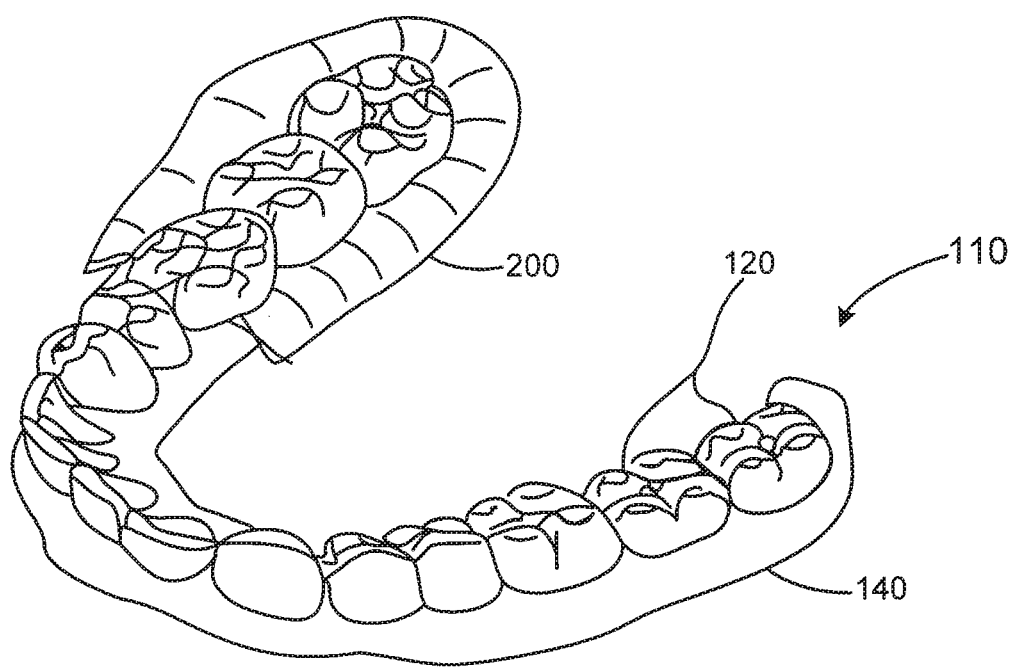
FIG. 2 illustrates a diagram illustrating a partial model of a patient's dentition, including a model of gingival tissue.

FIG. 2 is a diagram illustrating a portion of a typical digital dentition model 110 derived from the IDDS. Dentition model 110 includes models of individual teeth 120 and a model of the patient's gums 140. Various techniques for creating models of gum tissue and individual teeth from the IDDS are described in, for example, U.S. patent application Ser. Nos. 09/264,547 and 09/311,941.

Furthermore, FIG. 2 shows a portion of another gingival model 200 (a "secondary" gingival model), which is constructed to overlie gingival model 140 derived from the IDDS (the "primary" gingival model). The program uses the secondary gingival model 200 to model the deformation of the gingival tissue around the patient's teeth as the teeth move from their initial positions to their final positions. This ensures that orthodontic appliances made from positive molds of the patient's dentition fit comfortably around the patient's gums at all treatment stages. The secondary gingival model 200 also adds thickness to the gum model, which ensures that the orthodontic appliances do not press too tightly against the patient's gums.

Reference will now be made to various exemplary embodiments of the invention, which are illustrated in the accompanying figures. While these exemplary embodiments are described in sufficient detail to enable those skilled in the art to practice the invention, it should be understood that other embodiments may be realized and that logical and/or mechanical changes may be made without departing from the spirit and scope of the invention. Thus, the various embodiments herein are presented for purposes of illustration and not by way of limitation. For example, the steps recited in any of the method or process descriptions may be executed in any order and are not limited to the order presented. Moreover, any of the functions or steps may be outsourced to or performed by one or more third parties.

For the sake of brevity, conventional data networking, application development, and other functional aspects of the systems (and components of the individual operating components of the systems) may not be described in detail herein. Furthermore, the connecting lines shown in the various figures contained herein are intended to represent exemplary functional relationships and/or physical connections between the various elements. It should be noted that many alternative and/or additional functional relationships or physical connections may be present in a practical system.

Various embodiments of the present invention include one or more computing devices having programs stored therein for staging the movement of a patient's teeth. The computing device(s) or various components of any computing device discussed herein may include one or more of the following: a host server or other computing systems including a processor for processing digital data; a memory coupled to the processor for storing digital data; an input digitizer coupled to the processor for inputting digital data; an application program stored in the memory and accessible by the processor for directing processing of digital data by the processor; a display device coupled to the processor and memory for displaying information derived from digital data processed by the processor; and a plurality of databases. Various file indexes and/or databases used herein may include: client data; merchant data; and/or other similar useful data.

As those skilled in the art will appreciate, any computing device utilized by a user may include an operating system (e.g., Windows NT, 95/98/2000, OS2, UNIX, Linux, Solaris, MacOS, etc.) as well as various conventional support software and drivers typically associated with computers. As will be appreciated by one of ordinary skill in the art, each computing device may be embodied as a customization of an existing system, an add-on product, upgraded software, a stand alone system, a distributed system, a method, a data processing system, a device for data processing, and/or a computer program product. Accordingly, any program stored therein may take the form of an entirely software embodiment, an entirely hardware embodiment, or an embodiment combining aspects of both software and hardware. Furthermore, any program may take the form of a computer program product on a computer-readable storage medium having computer-readable program code means embodied in the storage medium. Any suitable computer-readable storage medium may be utilized, including hard disks, CD-ROM, optical. storage devices, magnetic storage devices, and/or the like.

In accordance with an exemplary embodiment, a computing device is configured to receive an electronic representation of the patient's teeth in an initial position taken by, for example, an intra-oral scanner (i.e., a CT scanner) based on an impression or partial impression of the patient's teeth. In addition, the computing device is configured to receive or generate an electronic representation of a desired final position for each of the patient's teeth. The program stored within the computing device is configured to analyze the initial and final positions, and automatically create a route for each tooth to move from its initial position to its final position. A set of aligners to move the teeth along the path in various stages is manufactured for the patient. As the patient wears the aligners, the patient's teeth move along the path according to each stage.

With certain patients, it is desired to use conventional brackets and wire, instead of the aligners, for one or more stages. This invention contemplates positioning brackets, e.g., virtual 3D brackets, for any stage during the movement of the teeth, including using brackets for all stages. As each patient's teeth and other factors differ, it may be that treatment is started with brackets and wire and then finished with aligners for some patients, while other patients may start with aligners, switch to brackets and wire, and may even switch back to aligners to finish the treatment. Alternatively, other patients may use brackets and wire for all stages of treatment.

Figure 3A:
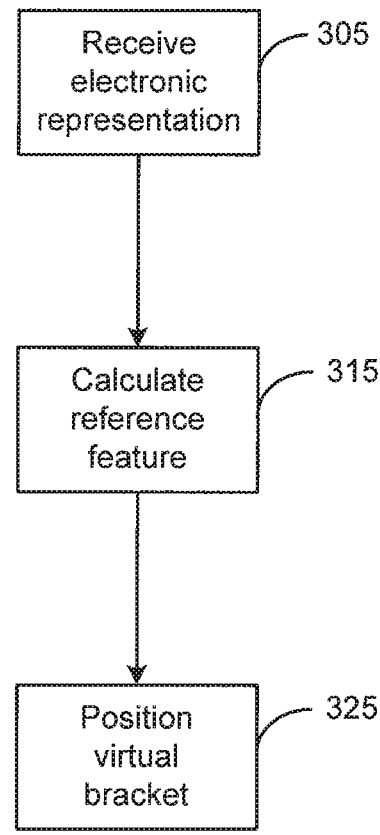
FIG. 3A illustrates a flow diagram illustrating an exemplary process for positioning virtual 3D brackets.

In accordance with various aspects of the present invention, a system and method for positioning virtual 3D brackets on teeth in a virtual 3D jaw pair model are provided, wherein the virtual 3D brackets may be used to precisely position brackets and wire for specific stages of treatment. For example, FIG. 3A illustrates a flow diagram for an exemplary process for positioning virtual 3D brackets on teeth in a virtual 3D jaw pair model. An electronic representation, in three dimensions, of the teeth is received at a host computer (305). Various reference features are calculated (315) from the received three dimensional data. Virtual 3D brackets are then positioned on the teeth in the virtual 3D jaw pair model by utilizing one or more of the calculated reference features (325). Reference to these steps will be made in the detail description that follows.

Figure 3B:
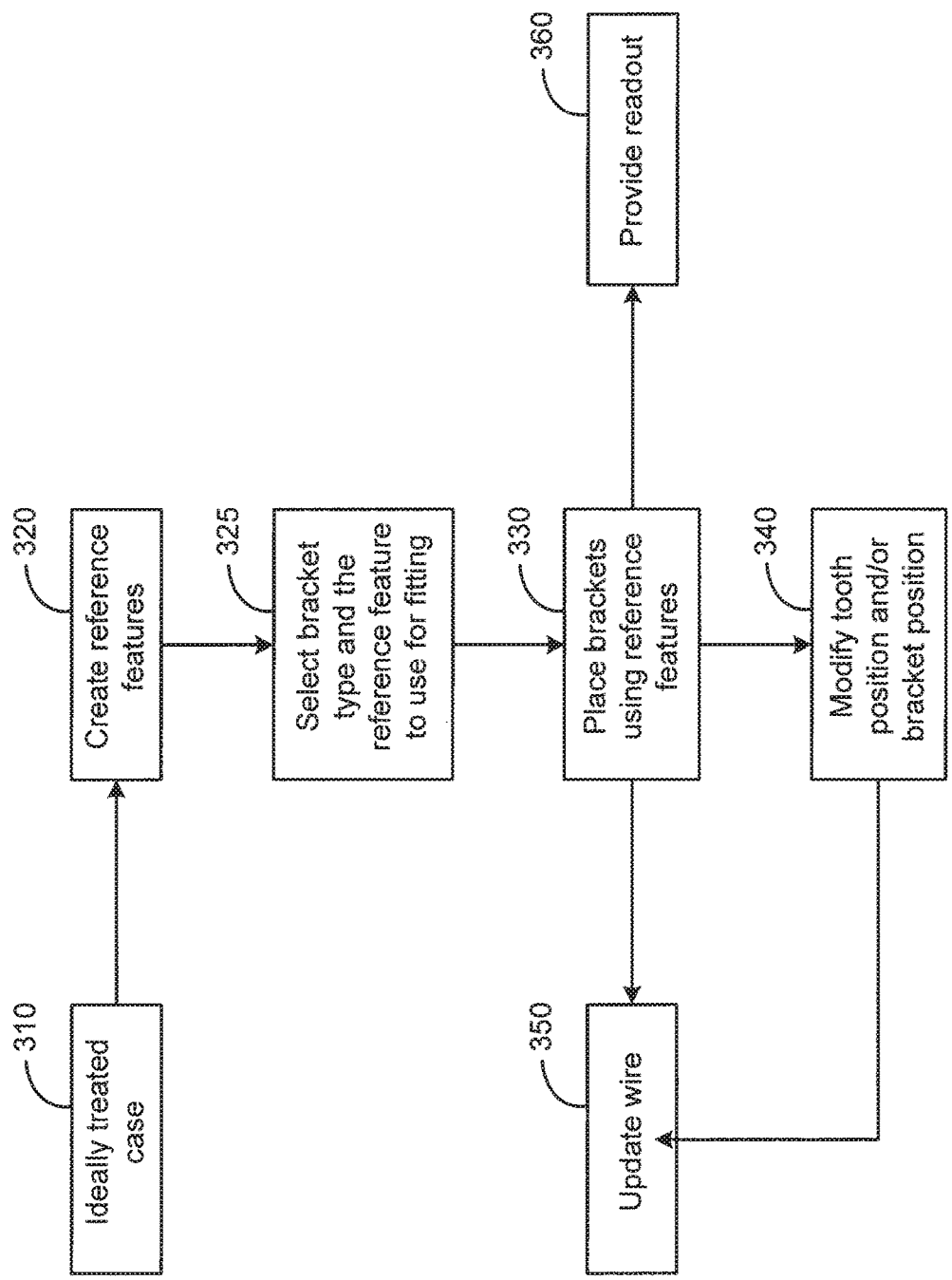
FIG. 3B illustrates a flow diagram illustrating an exemplary process for positioning virtual 3D brackets.

FIG. 3B illustrates a flow diagram for another exemplary process for positioning virtual 3D brackets on teeth in a virtual 3D jaw pair model. A set of reference features are created (320) from an ideally treated case (310). A reference feature and bracket type may be selected for the bracketing positioning process (325). Virtual 3D brackets are then positioned on the teeth in the virtual 3D jaw pair model by utilizing the created reference features (330). After the initial placement of the brackets, a user of the system can modify the position of any virtual tooth and virtual bracket (340) through intermediate and final stages for wearing the brackets. The display of the wire can also be updated so that the user can see the flow of the wire through the slots of the virtual brackets (350). In addition, a report that provides information on the wire deviation from the initial to the final stages can also be provided (360).

Figure 5:
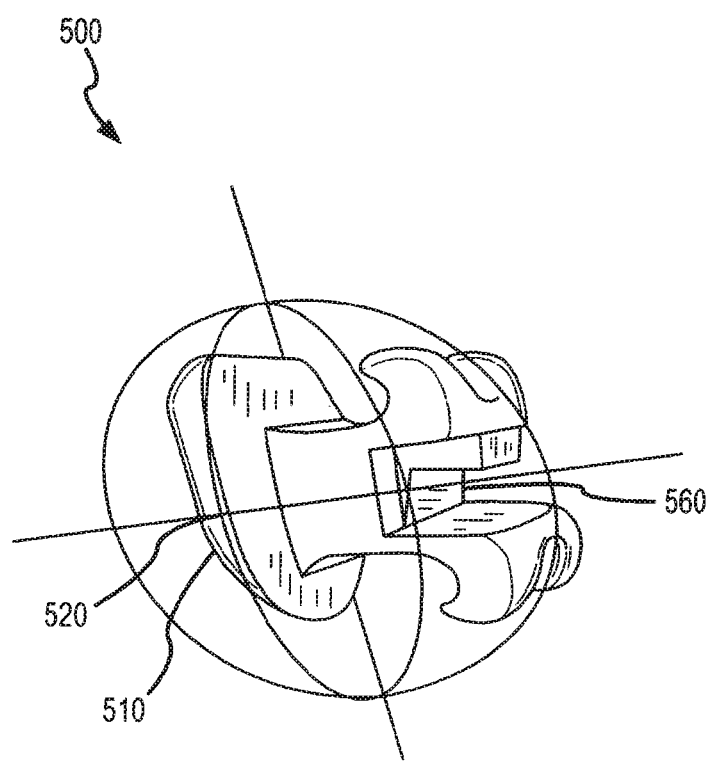
FIG. 5 illustrates an exemplary virtual bracket.

FIG. 5 illustrates an exemplary virtual bracket 500 that includes a bracket base 510, a base point 520, and a bracket slot 560 for holding a brace wire. A virtual bracket is suitably selected from a library of virtual brackets. In accordance with an exemplary embodiment, the virtual bracket is a 3D model of an existing bracket. A library of virtual brackets is generated from computer aided design (CAD) models, from existing brackets that are scanned, or from other sources of 3D data such as digitizing an existing bracket. In accordance with one aspect of an exemplary embodiment, for each bracket 500, bracket base 510 and base point 520 are accurately defined. Base point 520 is suitably located near the center of bracket base 510, with the origin of the axis center also at base point 520. The definition of bracket base 510 may include a bracket base contour that contains information about the shape (i.e., outline) of the bracket base. The slot and base inclinations may also be used by the user to select and position the virtual bracket. In addition, the base-point-to-slot-point distance and the width of the slot 560 may also be used to select and position the virtual bracket.

Figure 6A:
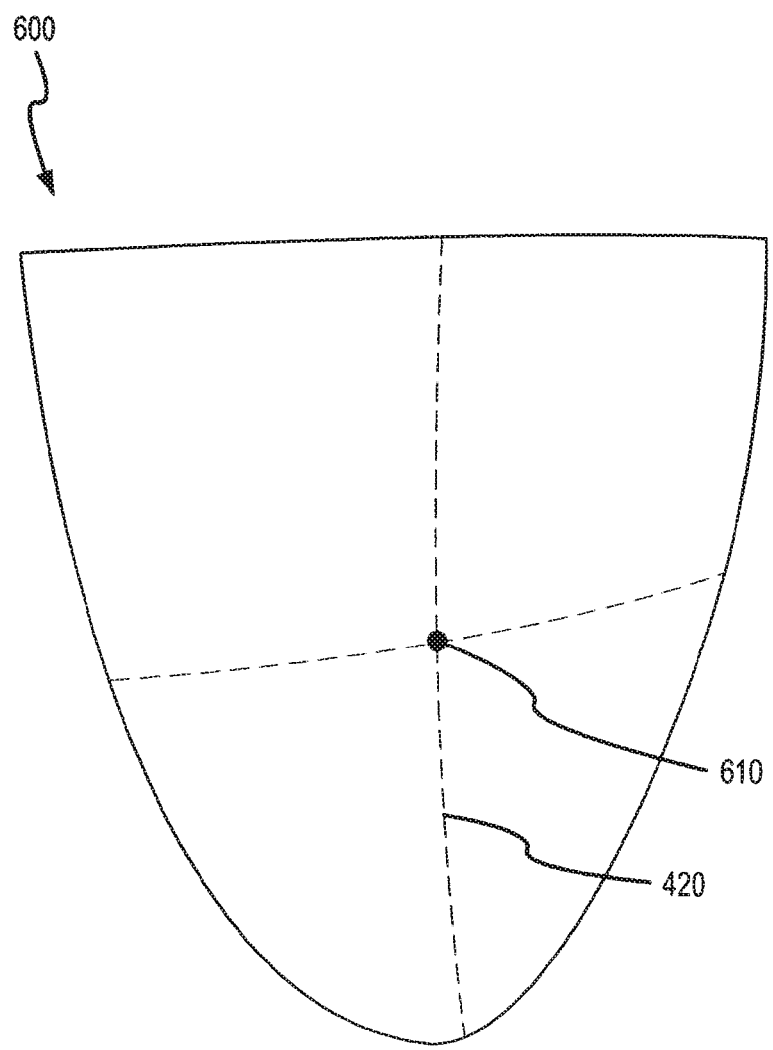
FIG. 6A illustrates the surface of an exemplary tooth.
Figure 6B:
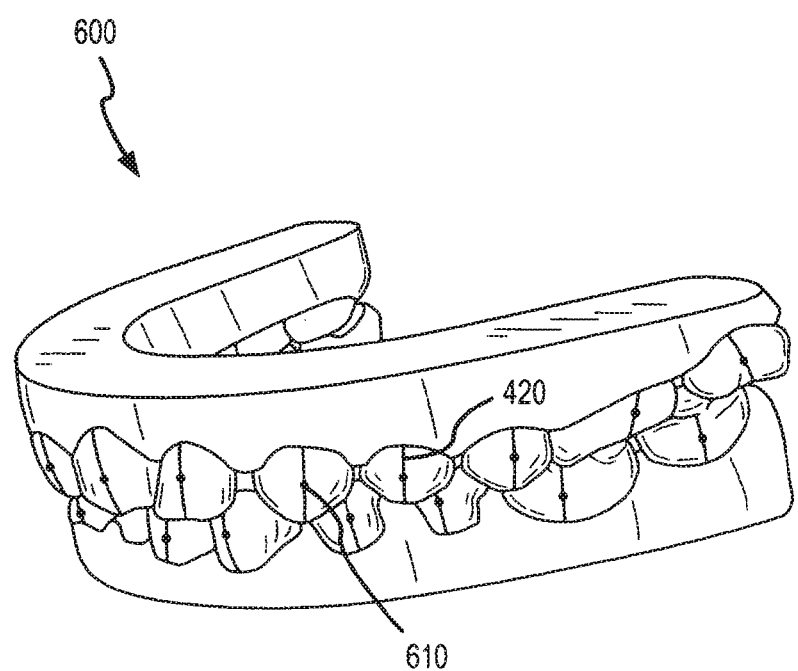
FIG. 6B illustrates exemplary FACCs on teeth.

After a type of virtual bracket is selected, a suitable site is located for the bracket's placement. FIGS. 6A and 6B illustrate a representative tooth 600 with FACC 420 and a facial axis (FA) point 610. Naturally, the area around FA point 610 on the tooth surface is a suitable candidate site for the bracket. However, other factors such as gingival or opposing teeth during occlusion may preclude this location. In an optimal positioning, the middle of each bracket site shares the same plane or surface when the teeth in an arch are optimally positioned. As described below, the program utilizes various criteria to ensure that the bracket 'sits' correctly on the tooth.

Figure 4:
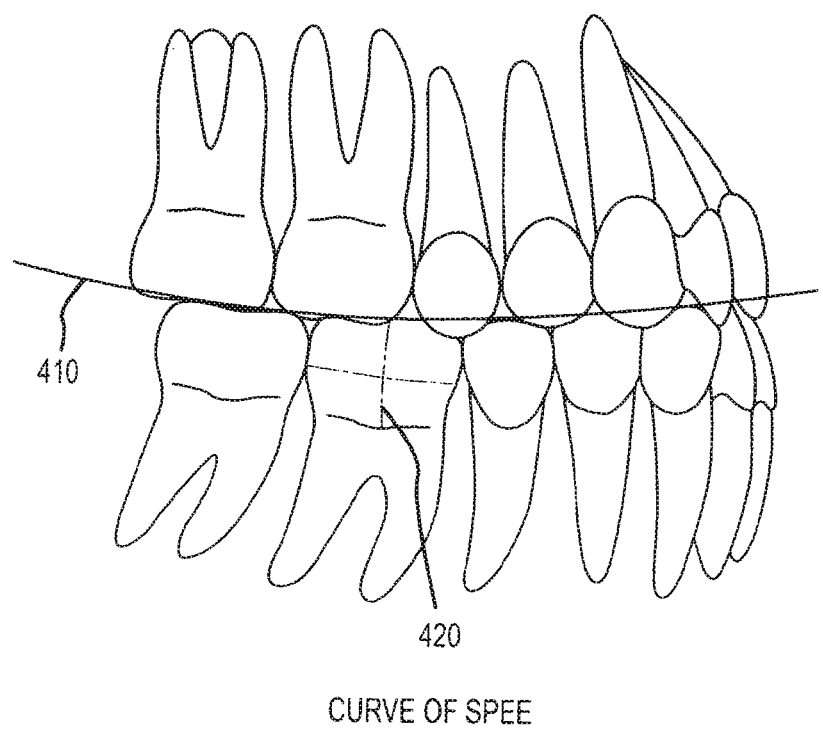
FIG. 4 illustrates exemplary reference features for calculating the placement of a virtual bracket.

As mentioned above and with reference to FIGS. 4 and 8, in an exemplary embodiment, reference features are created (steps 305, 320) to aid in the placement of the virtual brackets (steps 325, 330) and the creation of the wire that connects the brackets together. Exemplary reference features include the curve of Spee 410 (also known as compensating curve), Andrew's plane 810, and the facial axis of the clinical crown (FACC) 420. In accordance with an exemplary embodiment, Andrew's plane comprises the surface or plane on which the midtransverse plane of every crown in an arch will fall when the teeth are optimally positioned.

As described below, the reference features can be used to provide a reference plane for the virtual brackets to move along and to calculate various statistics such that a bracket may be precisely positioned on the tooth. Exemplary statistics include the aforementioned tip (angulation) and torque (inclination) of the brackets as described next.

Figure 10:
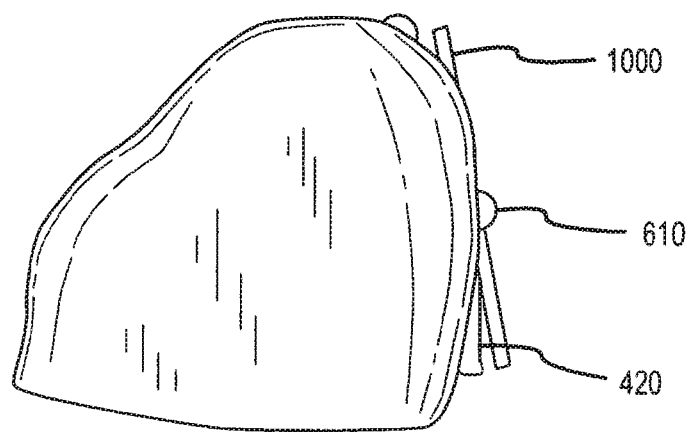
FIG. 10 illustrates an exemplary FACC feature set.

With reference to FIG. 6B, FACCs 420 may be used for automatically positioning of virtual brackets on the teeth. The user can draw FACC 420 on the clinical crown facial surface of each tooth that is to receive a bracket. With reference to FIG. 10, an FACC feature set may be calculated for each tooth that includes FA point 610 (i.e., center of the FACC), tangent direction 1000 of the FACC, and the normal direction of the FACC (i.e., normal that is coming out of the tooth). By using FA point 610 on each tooth, a list of neighboring triangles may be identified on the surface of each tooth that are within range of the bracket base profile. The range may be a configurable parameter that is read from a parameter file or interactively supplied by the user. In accordance with one embodiment of the present invention, the range may be based on the size of the bracket. For example, a larger bracket will result in a bigger range size than a smaller bracket.

For an initial position of the bracket, the program aligns the bracket with the FACC tangent and normal directions. The program uniformly samples points on the bracket base profile, and for each sample point, finds the closest point on the neighbor surface from the list of triangles to form two point sets. The program then performs point cloud matching to find the best least square fit transform between the two point sets.

Since the best fitting might induce collision of the bracket and tooth at the fitting site, a few extra iterative steps are taken to move the bracket away from the tooth by a faction of the collision amount. The end resulting transform is used for the final bracket fitting.

Figure 8:
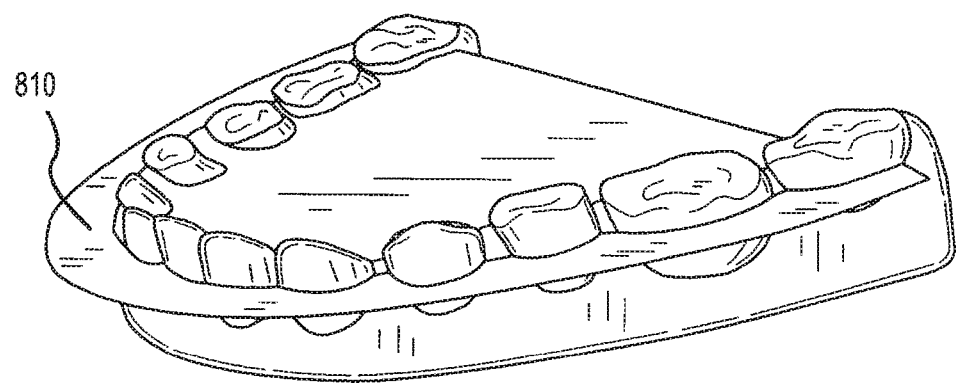
FIG. 8 illustrates an exemplary Andrew's plane on a lower jar.

With reference to FIG. 8, Andrew's plane 810 can be used to define a planar surface for positioning brackets on teeth. As illustrated in FIG. 8, the initial position of Andrew's plane 810 is a plane that is a best fit through the centers of the clinical crown facial surface of each tooth. Bracket slots 560 are lined up to be positioned on the surface of Andrew's plane 810. The program calculates the intersection of Andrew's plane 810 and the FACC curve and uses the intersecting points to identify a list of neighboring triangles on the surface of the tooth that are within range of the bracket base profile.

The program aligns the bracket in the up and out directions with the Andrew's plane normal up and FACC normal directions. The program uniformly samples points on the bracket base profile, and for each sample point, finds the closest point on the neighbor surface from the list of neighboring triangles to form two point sets. The program then performs point cloud matching to find the best least square fit transform between the two point sets.

The previous step fits the bracket base with the tooth, however, the bracket slot might not be lined up on the Andrew's plane surface, so the program then performs iterative steps to adjust the slot point position to be on the Andrew's plane, which defines a new possible fitting site, and the align and sample steps are repeated until the slot is within tolerance to the plane. The program may perform a few extra iterative steps to move the bracket away from the tooth to avoid collision. The end resulting transform is used for the final bracket fitting.

Figure 9:
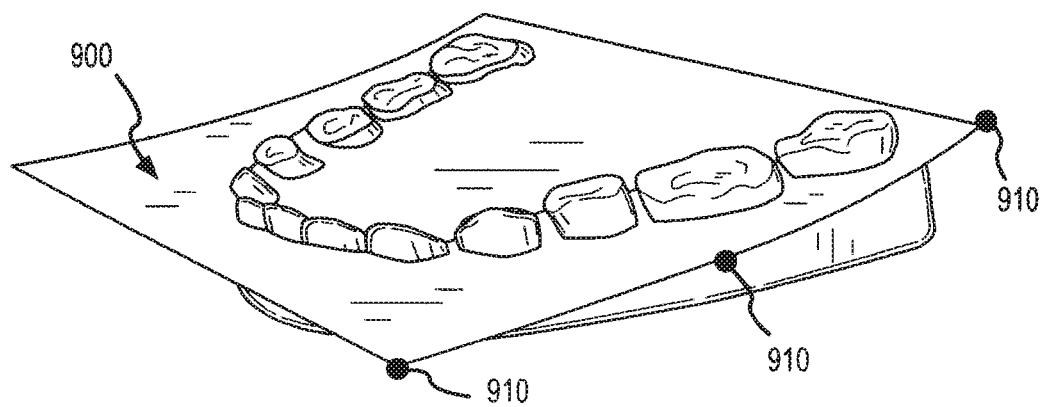
FIG. 9 illustrates an exemplary curve of spee on a lower jar.

With reference to FIG. 9, the curve of Spee can be used to define a flexible surface 900. As illustrated, flexible surface 900 can be initially positioned by the program to pass through the center of the crowns of the teeth. Control points, such as control points 910, can be modified by the user to change the shape of the surface to form a concave or convex surface.

Bracket slots 560 are lined up to be positioned on the surface of flexible surface 900. The program calculates the intersection of flexible surface 900 and the FACC curve and uses the intersecting points to identify a list of neighboring triangles on the surface of the tooth that are within range of the bracket base profile.

The program aligns the bracket in the up and out directions with the flexible surface normal up and FACC normal directions. The program uniformly samples points on the bracket base profile, and for each sample point, finds the closest point on the neighbor surface from the list of neighboring triangles to form two point sets. The program then performs point cloud matching to find the best least square fit transform between the two point sets.

The previous step fits the bracket base with the tooth, however, the bracket slot might not be lined up on flexible surface 900, so the program then performs iterative steps to adjust the slot point position to be on flexible surface 900, which defines a new possible fitting site, and the align and sample steps are repeated until the slot is within tolerance to flexible surface 900. The program may perform a few extra iterative steps to move the bracket away from the tooth to avoid collision. The end resulting transform is used for the final bracket fitting.

Orthodontic brackets are designed and produced with a fixed base profile for a given manufacturer prescription, and usage. The bracket base is the surface that interfaces with the tooth. Since a patient's tooth morphologies are unique, the bracket base and its underlying tooth may not mate well. Typically, a gap exists between the bracket base and the tooth surface. This gap needs to be filled to form a "Custom Base". The custom base may involve adjusting the tip (angulation) and/or torque (inclination) of the bracket base when it is applied to the tooth.

In accordance with an exemplary embodiment, the reference features are created automatically and cannot be modified by the user. In accordance with another exemplary embodiment, the reference features may be modified by the user by manipulating characteristics of the reference features such as the curvature of the curve of Spee 410.

During determination of the bracket's location, the program also takes into account the possibility of collisions between brackets and teeth and gingival, especially when brackets are situated in the earlier stages.

In accordance with an exemplary embodiment, the user can specify a specific stage for starting the bracket placing calculation and a specific stage for ending the bracket placing calculating. It should be appreciated that this provides for additional freedom of treatment, such as starting a treatment with brackets and wire first, and then finishing with aligners, or vice versa. In addition, the user can specify specific teeth that will receive a bracket, as there are cases where only a subset of the teeth receive brackets.

After the initial placement of the bracket by the program, users may modify any tooth and bracket position. Teeth can be manipulated freely, while the bracket is restricted to move on the surface of tooth or to move such that the direction of the bracket is aligned with the reference plane normal of the tooth. In accordance with an exemplary embodiment, the bracket may also be moved such that it slides on the reference surface while still attached to the tooth. After the user modifies the position of the teeth and brackets, the program tests for collision of brackets and teeth to make sure the newly modified position will not result in any collisions.

At any time during or after the positioning of the teeth and brackets, the program can display the wire, which follows the slots of the virtual brackets.

After the placement of the virtual brackets, the program outputs a wire deviation that includes information such as bracket tip, torque angles and shift, and wire length. In accordance with one embodiment of the invention, if a projection direction is input into the program, a 2D projection of the wire shape at the initial and final stages can also be output.

Once the position of the virtual brackets is finalized, a dental template may be created to facilitate the positioning of the "real" brackets on the patient's teeth. An exemplary dental template is described in U.S. patent application Ser. No. 10/794,324.

Figure 7A:
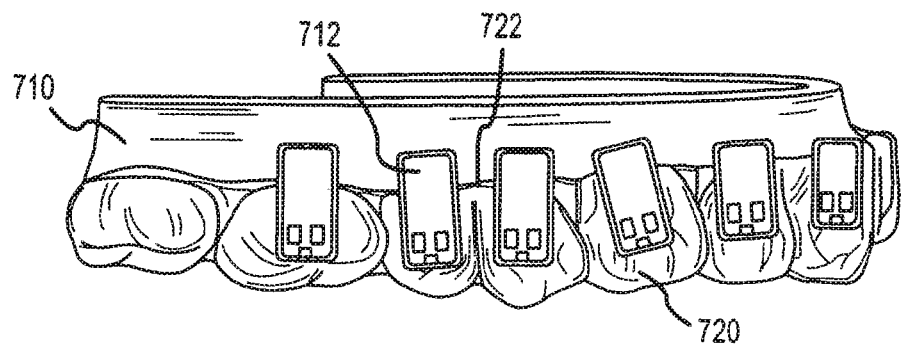
FIGS. 7A-C illustrate perspective views of various dental templates.

For example, FIG. 7A illustrates an exemplary dental template 720 or appliance formed over a mold 710. The template is similar in appearance to a removable appliance; however, it has openings 722 or "port-holes" approximating key portions of the footprint and/or other geometrical features of a bracket to guide the precise placement of the bracket on its respective tooth.

Figure 7B:
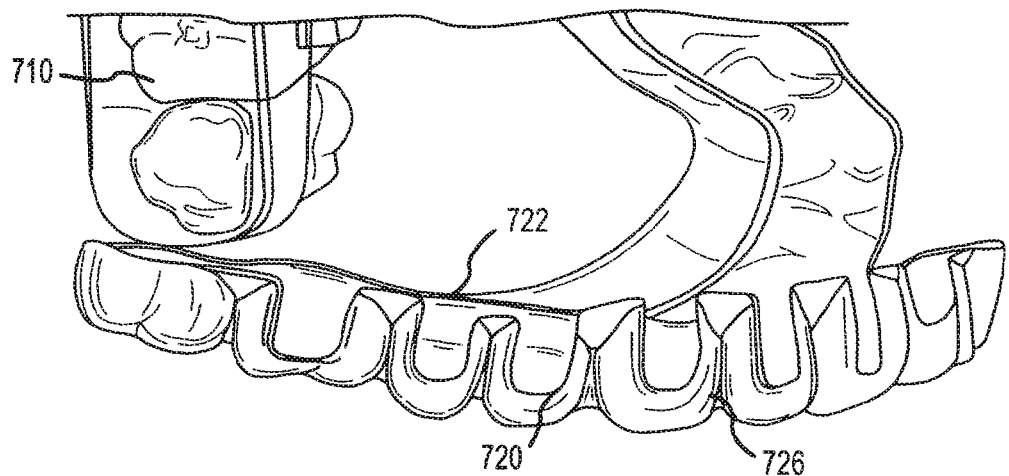

Mold 710 is a physical rendition of a digital model that has been fabricated using rapid prototyping methods. A bump or projection 712 rises from mold 710 so when the dental template or appliance is thermal-formed, an opening 722 is formed on the template 720. The opening 722 is where the template is cut out along the edge of the bump or projection 712. The opening 722 has a brace support edge 726, whose operation is illustrated in FIG. 7B. In addition to the support edge 726, the template 720 may have features that will minimize the retention of it on the dental anatomy. For example, the lingual side of the device may not have maximum coverage.

Turning now to FIG. 7B, template 720 is separated from the mold 710. The opening 722 allows a bracket base to fit into the opening 722. Brace support edge 726 is needed to securely position the bracket in the template 720. In this embodiment, the brace support edge 726 is curvaceous. If edge 726 had been terminated as a simple flat edge, the bracket can be located in X and Y surfaces on the tooth, but the Z direction (buccal lingual direction) would not be controlled. Edge 726 provides the needed control of the bracket's degree of freedom in the Z direction to allow orientation of the bracket about any given axis. Those features allow the bracket to be secured in the proper position and orientation on its respective tooth. Edge 726 can change, depending on vendor-to-vendor or prescription-to-prescription.

Figure 7C:
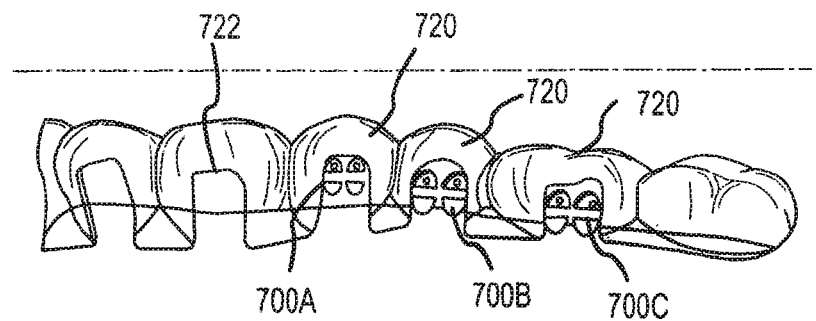

FIG. 7C illustrates a template wherein each of the openings, cut-outs, port-holes, or slots 722 in the template 720 are designed to fit particular brackets 700A, 700B and 700C, each of which fits into its respective portion on the template.

Additional information on dental templates and various techniques for creating dental templates are described in U.S. patent application Ser. No. 10/794,324.

Benefits, other advantages, and solutions to problems have been described herein with regard to specific embodiments. However, the benefits, advantages, solutions to problems, and any element(s) that may cause any benefit, advantage, or solution to occur or become more pronounced are not to be construed as critical, required, or essential features or elements of any or all the claims or the invention. The scope of the present invention is accordingly to be limited by nothing other than the appended claims, in which reference to an element in the singular is not intended to mean "one and only one" unless explicitly so stated, but rather "one or more." All structural, chemical, and functional equivalents to the elements of the above-described exemplary embodiments that are known to those of ordinary skill in the art are expressly incorporated herein by reference and are intended to be encompassed by the present claims.

What is claimed is:

1. A method for positioning virtual brackets on a virtual representation of a patient's teeth, the method comprising:
   generating an electronic representation of the patient's teeth by obtaining scan data from a scanner's scanning of the patient's teeth and generating a model derived from the scan data of the patient's teeth;
   outputting, with a display, the virtual representation of the patient's teeth, the virtual representation of the patient's teeth being based on the electronic representation of the patient's teeth;
   determining facial axis points of one or more of the patient's teeth from the outputted electronic representation of the patient's teeth;
   determining a reference plane relative to the electronic representation of the patient's teeth;
   outputting, with the display, the reference plane relative to the virtual representation of the patient's teeth;
   outputting, with the display, control points, wherein the control points are manipulable by a user for modifying an anatomic reference plane;
   locating sites for placement of virtual brackets on the virtual representation of the patient's teeth based on at least the determined facial axis points of the patient's teeth; and
   outputting, with the display, the virtual brackets on the virtual representation of the patient's teeth in an initial position, the virtual brackets aligned on the virtual representation of the patient's teeth according to the reference plane.

2. The method of claim 1, further comprising, receiving user input via at least one of the control points to manipulate the control point.

3. The method of claim 2, further comprising:
   modifying the reference plane relative to the virtual representation of the patient's teeth to form a modified reference plane; and
   after modifying the reference plane, outputting, with the display, the reference plane relative to the virtual representation of the patient's teeth.

4. The method of claim 1, further comprising, prior to outputting the virtual brackets on the virtual representation of the patient's teeth, receiving a user selection of a virtual bracket type from a library of virtual brackets; and wherein virtual bracket base contours of the user selected virtual bracket type are defined.

5. The method of claim 4, wherein outputting the virtual brackets on the virtual representation of the patient's teeth comprises aligning virtual brackets with respective sites and calculating a final bracket fitting for each virtual bracket based at least on the virtual bracket base contour of the respective virtual bracket, wherein the final bracket fitting for each virtual bracket avoids collision of each virtual bracket and respective patient's teeth.

6. The method of claim 1, further comprising calculating angulation and inclination statistics of the positioned virtual brackets using the reference plane.

7. The method of claim 1, wherein the reference plane is created from an ideally treated case associated with the electronic representation of the patient's teeth.

8. The method of claim 1, further comprising:
displaying a wire extending through the virtual brackets;
receiving user input comprising at least one of a user modification of a position of a virtual tooth of the displayed virtual representation of the patient's teeth or a user modification of a position of an outputted virtual bracket; and
updating the display of the displayed wire in response to the user input.

9. The method of claim 1, wherein determining the reference plane comprises receiving a user selection of the reference plane.

10. The method of claim 1, wherein the reference plane comprises Andrew's plane or the curve of Spee.

11. The method of claim 1, further comprising finalizing positions of the virtual brackets on the virtual representation of the patient's teeth and outputting instructions for fabricating a dental template to facilitate positioning of real brackets on the patient's teeth.

12. The method of claim 1, further comprising modifying the initial position of the virtual bracket on the patient's tooth in response to input from a user.

13. The method of claim 12, wherein modifying the initial position of the virtual bracket comprises one or more of: restricting the virtual bracket to move on a surface of the patient's tooth or restricting the virtual bracket to move along the reference feature.

14. The method of claim 12, further comprising testing for a collision of the virtual bracket with the patient's tooth.

15. The method of claim 1, wherein the virtual representation of the patient's teeth represents the patient's teeth in a target arrangement.

16. A method comprising:
generating an electronic representation of a patient's teeth by obtaining scan data from a scanner's scanning of the patient's teeth and generating a model derived from the scan data of the patient's teeth;
receiving an electronic representation of the patient's teeth, the electronic representation being formed from an output of the scanner used to scan the patient's teeth;
outputting, with a display, the virtual representation of the patient's teeth, the virtual representation of the patient's teeth being based on the electronic representation of the patient's teeth on the display;
determining an anatomic reference plane relative to the electronic representation of the patient's teeth, the anatomic reference plane being defined in part by reference points on the patient's teeth;
outputting, with the display, the anatomic reference plane;
outputting, with the display, control points for modifying the anatomic reference plane;
outputting, with the display, virtual brackets on the virtual representation of the patient's teeth, the virtual brackets aligned on the virtual representation of the patient's teeth according to the anatomic reference plane; and
finalizing positions of the virtual brackets on the virtual representation of the patient's teeth.

17. The method of claim 16, further comprising receiving a user input to at least one of the control points for modifying a shape of the anatomic reference plane, wherein the user input is received through user manipulation of one or more of the control points.

18. The method of claim 16, wherein:
the virtual representation of the patient's teeth includes a virtual representation of the patient's gingival tissue; and
the finalized positions of the virtual brackets on the virtual representation of the patient's teeth accounts for collisions between the virtual brackets and the virtual representation of the patient's teeth and gingival tissue.

19. A system for positioning a virtual bracket on a virtual representation of a patient's tooth, the system comprising:
a scanner; and
memory comprising program code that, when executed by a processor, causes the system to:
receive an electronic representation of the patient's tooth, the electronic representation being formed from an output of the scanner used to scan the patient's teeth;
output, with the display, the virtual representation of the patient's teeth, the virtual representation of the patient's teeth being based on the electronic representation of the patient's teeth;
determine a reference point of the patient's tooth from the received electronic representation of the patient's tooth;
determine a reference plane relative to the received electronic representation of the patient's tooth;
output the reference plane on the display;
output control points on the display;
receive a user input for modifying the reference plane via the control points;
modify a shape of the reference plane based on the user input;
locate a site for placement of the virtual bracket on the virtual representation of the patient's tooth based on at least the reference point of the patient's tooth;
output, with the display, the virtual bracket on the virtual representation of the patient's tooth, the outputted virtual bracket aligned on the virtual representation of the patient's tooth based on at least the modified reference plane; and
finalize a position of the virtual bracket on the virtual representation of the patient's tooth.

20. The system of claim 19, wherein the reference point comprises a facial axis point of the patient's tooth.

21. The system of claim 19, wherein the scanner is an intraoral scanner.

* * * * *